United States Patent [19]
Sukigara et al.

[11] Patent Number: 4,622,464
[45] Date of Patent: Nov. 11, 1986

[54] INFRARED GAS ANALYZER

[75] Inventors: Kunio Sukigara; Harutaka Taniguchi, both of Yokosuka, Japan

[73] Assignees: Fuji Electric Co., Ltd.; Fuji Electric Corporate Research & Development Ltd., both of Japan

[21] Appl. No.: 672,091

[22] Filed: Nov. 15, 1984

[30] Foreign Application Priority Data

Nov. 15, 1983 [JP] Japan ................. 58-214442

[51] Int. Cl.[4] ................ G01J 1/00; 250 343; 356 437; 356 439; 356 440
[52] U.S. Cl. .................... 250/343; 356/439
[58] Field of Search ................................ 1/6

[56] References Cited

U.S. PATENT DOCUMENTS 2,468,740  5/1949  Else ............................ 356/439
3,826,918  7/1974  Van Der Koogh et al. ....... 250/343
4,225,243  9/1980  Typpo ........................... 356/439

Primary Examiner—Janice A. Howell
Attorney, Agent, or Firm—Brumbaugh, Graves, Donohue & Raymond

[57] ABSTRACT

In the infrared gas analyzers described in the specification, infrared radiation is transmitted through a measuring cell to an infrared detector. The measuring cell has an external case and a tubular filter to remove particulate material from the gas being analyzed immediately before it is intercepted by the infrared radiation.

6 Claims, 10 Drawing Figures

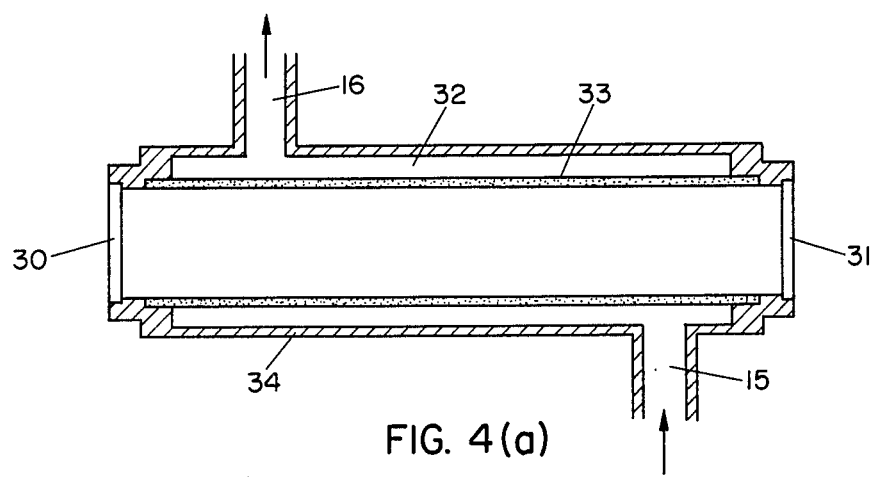
FIG. 4(a)
FIG. 4(b)
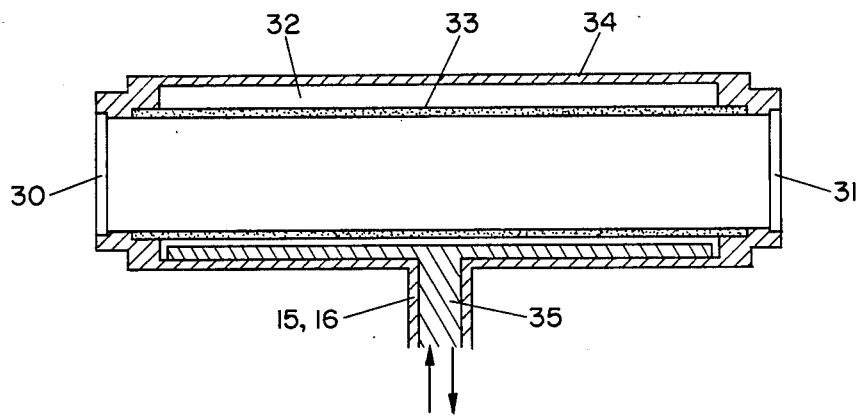
FIG. 5(a)
FIG. 5(b)

INFRARED GAS ANALYZER

BACKGROUND OF THE INVENTION

This invention relates to infrared gas analyzers for measuring the concentration of a gas being examined by infrared absorption and, more particularly, to a new and improved infrared gas analyzer for directly and continuously measuring gas concentration within a smoke duct.

Infrared gas analyzers may be classified into analyzers using optical systems of single and double beam types. Both types of optical systems include a light source, a measuring cell and a detector as principal components. When infrared gas analyzers are used to measure gas concentrations of gases containing particulate materials, such as smoke, the particulate material must be removed in order to prevent it from interfering with the measurement. Conventional arrangements for removing particulate material are time consuming and delay the determination of gas concentration by the infrared analyzer. In those instances where process control is based on the gas analysis, such delays in the determination can interfere with the process being carried out.

Accordingly, it is an object of the present invention to provide a new and improved infrared gas analyzer which overcomes the above-mentioned disadvantages of the prior art.

Another object of the invention is to provide an infrared gas analyzer in which particulate matter is removed from the gas being analyzed in a rapid and efficient manner without causing significant delay in the gas being analyzed.

BRIEF SUMMARY OF THE INVENTION

These and other objects of the invention are attained by providing an infrared gas analyzer comprising an infrared source, a measuring cell and an infrared detector wherein the measuring cell comprises a tubular filter within a tubular enclosure having infrared transmitting windows at opposite ends, the enclosure being arranged so that the gas to be analyzed flows into a space between the inner wall of the tubular enclosure and the tubular filter and from that space through the tubular filter to the interior thereof where it is interposed between the infrared source and the measuring detector. Particulate material is thus removed from the gas immediately prior to the infrared analysis so that the response time of the analyzer is substantially reduced.

BRIEF DESCRIPTION OF THE DRAWINGS

Further objects and advantages of the invention will be apparent from a reading of the following description in conjunction with the accompanying drawings, in which:

FIGS. 4(a) and 4(b) are views in longitudinal section and cross-section, respectively, of another embodiment of an infrared gas analyzer according to the present invention;

FIGS. 5(a) and 5(b) are views in longitudinal section and cross-section, respectively, illustrating a further embodiment of an infrared gas analyzer according to this invention.

DESCRIPTION OF PREFERRED EMBODIMENTS

Figure 1:
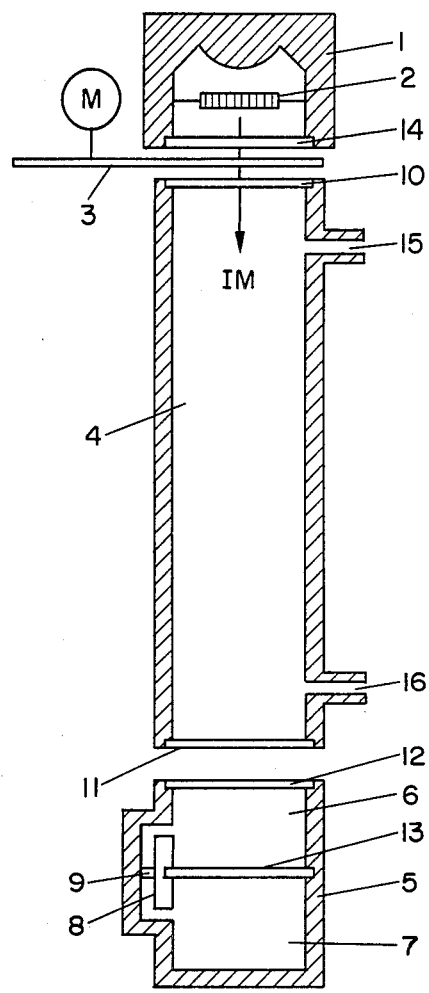
FIG. 1 is a longitudinal sectional view illustrating a conventional single beam-type infrared gas analyzer.

Referring now to FIG. 1 to facilitate an understanding of the present invention, the operational principle of an infrared gas analyzer of the single beam type will be described briefly. In FIG. 1, radiant flux IM radiated from an infrared radiator 2 in a light source 1 passes through a measuring cell 4 after being intermittently interrupted by a sector disc 3. The measuring cell 4 has infrared transmission windows 10 and 11 at each end an inlet 15 and an outlet 16 for a gas to be analyzed, the gas normally being introduced into the cell through the inlet 15. The radiant flux IM is partially absorbed by the gas being examined within the measuring cell 4 and is then transmitted to a detector 5 positioned adjacent to the window 11 at the other end of the cell 4. The detector 5 has a first detection chamber 6 and a second detection chamber 7 each arranged to hold a portion of the gas being analyzed, and a passage 8 connecting the chambers 6 and 7. The radiant flux IM which enters the detector is partially absorbed in the first detection chamber 6 and is then further absorbed in the second detection chamber 7. The difference between the increase in pressure $\Delta P$ caused by the absorption of the radiant flux IM by the component gas being examined in the first detection chamber 6 and the increase caused by the absorption in the second detection chamber 7 is detected by a pressure difference detection element 9 which produces a corresponding electrical signal.

In the measuring cell 4, into which a gas containing particulate matter, such as a combustion exhaust gas, is introduced, it will be assumed that the lengths of the light paths in the first and second detection chambers, respectively, are $l_1$ and $l_2$, the volumes of the chambers are $V_1$ and $V_2$, the changes in pressure are $\Delta P_1$ and $\Delta P_2$, the concentration of the gas in the detection chambers is $C_o$, the radiant intensity of the source at the central wavelength of the absorption band of the component gas being analyzed is $IM(\lambda_1)$, the absorption of the component gas being examined at the central wavelength $\lambda_1$ is $\alpha M$, the light absorption coefficient of the particulate matter is $\beta M$, and the concentrations of the component of interest contained in the gas being examined of the dust are CM and CD, respectively. Then the output of the detector is represented approximately by the following expression:

$$S \propto (\Delta P_1 - \Delta P_2) \propto IM(\lambda_1)e - (\alpha MCM + \beta M + CD)\cdot l \propto IM(\lambda_1)\{1 - (\alpha MCM + \beta MCD)l\} \quad (1)$$

As seen from the expression (1), the output S is proportional to the concentration of the component gas being examined and an accurate measurement of the concentration of the component gas being examined is impossible unless the concentration of the particulate matter is known. Consequently, unless the particulate matter is removed, that quantity must be measured by another means.

Figure 2:
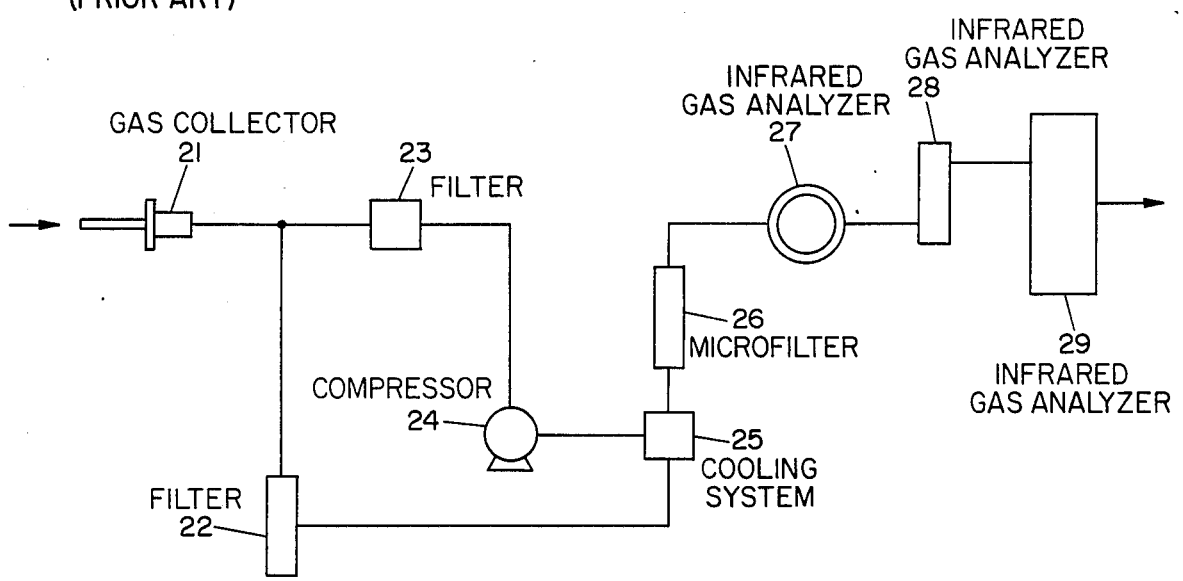
FIG. 2 is a schematic block diagram showing a typical sampling system arrangement in a conventional infrared gas analyzer.

When a conventional infrared gas analyzer is used to analyze a gas containing a considerable amount of particulate matter, such as is discharged from a gas duct, a gas purifying system is necessary to remove the particulate matter before the gas being analyzed is introduced in the measuring cell 4. FIG. 2 illustrates a typical conventional gas purifying system in which a gas collector 21 for collecting a gas being examined contains a first stage coarse filter for removing coarse particulate matter contained in the gas to be analyzed. The gas is then dried by condensation of moisture using a compressor 24 and cooling system 25 and any further particulate matter is removed by a second stage microfilter 26 immediately before being introduced into an infrared gas analyzer 27, 28, 29. The particulate matter is thus prevented from affecting the output signal of the infrared gas analyzer. This ensures that the concentration of the component gas being analyzed is accurately measured and the portion of expression (1) relating to the particulate matter may be eliminated.

Attempts are being made in various fields, however, to employ infrared gas analyzers not only for simply monitoring the content of various components in a gas but also to use the signals generated thereby as system control signals. In such cases, a high response speed is required in addition to high accuracy of the signal generated by the infrared gas analyzer. Although conventional infrared gas analyzers may provide a response speed substantially as high as is necessary to allow them to be used for system controlling purposes, it is necessary to use such gas sampling systems for analysis of gases containing particulate matter. As a result, the particulate matter must first be removed so that the response speed of the measuring system as a whole ranges from several tens of seconds up to the order of minutes and consequently such infrared gas analyzers cannot be used for system controlling purposes when the gas contains particulate matter.

Figure 3A:
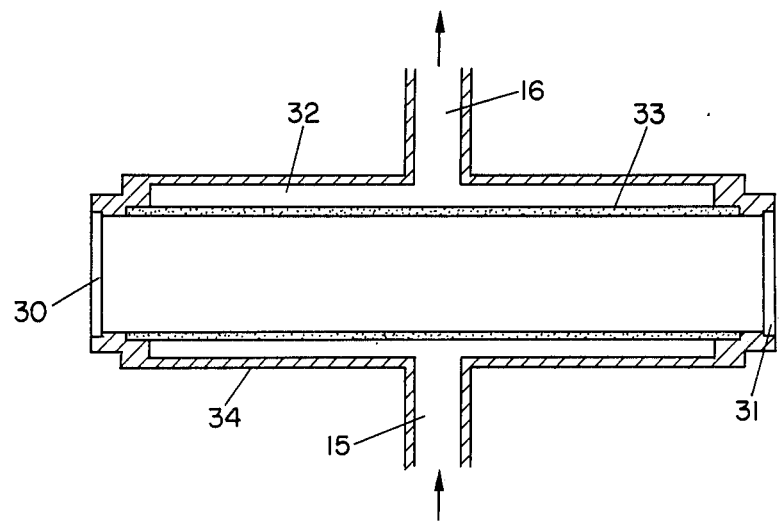
FIGS. 3(a) and 3(b) are views in longitudinal section and cross-section, respectively, illustrating a representative measuring cell for an infrared gas analyzer according to the present invention.
Figure 3B:
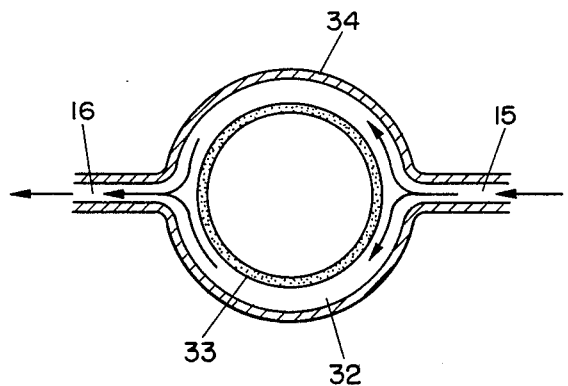

FIG. 3(a) illustrates a representative embodiment of an infrared gas analyzer embodying the present invention. In this embodiment, a measuring cell has infrared transmission windows 30 and 31, a tubular gas filter 33 and an external case 34 having a tubular internal wall. In FIG. 3(a), the tubular filter 33, which is a fibrous quartz tube or a ceramic porous sintered tube, is arranged so that it is removable from the external case 34 and a gas being examined is introduced into the interior of the cell only through the filter. The infrared transmission windows 30 and 31 each consist of an infrared transmissive material such as monocrystalline calcium fluoride and the external case 34 is arranged to provide a gas-tight seal. The external case 34 may be made of, for instance, metal, alloy or ceramics and is provided with an inlet 15 and an outlet 16 arranged on opposite sides to permit flow of the gas being analyzed through the case. In addition, a space 32, provided between the internal wall of the case and the tubular filter 33, extends in the longitudinal direction of the case so as to permit the unfiltered gas to flow outside the filter along the length of the cell. FIG. 3(b) illustrates the manner in which the gas being examined flows in the cross sectional direction of the measuring cell. As shown in FIG. 3(b) the flow of the gas being examined in this example, before filtering. The filtered gas will pass through the walls of the porous filter 33 into its interior and then be in the path of the infrared radiation directed through windows 30 and 31 is divided in half at the inlet 15, each half being directed around the circumference of the tubular gas filter 33, the paths joining at the outlet 16. This arrangement is particularly effective when the measuring cell is short.

FIG. 4(a) shows the longitudinal section of a second embodiment of the measuring cell of the invention. This embodiment is generally similar to the arrangement shown in FIGS. 3(a) and (b) except that the inlet 15 and the outlet 16 are spaced in the longitudinal direction of the measuring cell. FIG. 4(b) illustrates the flow of the gas being examined in the cross sectional direction of the measuring cell. As illustrated, the flow of the unfiltered gas being examined and introduced from the inlet 15 in this case is passed along outside of the tubular filter 33 and in the longitudinal direction of the filter. As before, the filtered gas will pass into the interior of the filter. This arrangement is particularly effective when the measuring cell is long.

FIG. 5(a) shows the longitudinal section of a third example of the measuring cell which is basically the same as that shown in FIG. 3 except that the inlet 15 and the outlet 16 are combined. in this example, a separator 35 separates the inlet and outlet paths and the gas being examined is caused to pass completely around the circumference of the tubular filter 33 between the inlet and the outlet paths to provide a faster response time. As before, the filtered gas will permeate into the interior of the filter 33. This arrangement is particularly effective when a poisonous gas, such as one containing a carbon monoxide as a component, is examined since the gas being analyzed must not be discharged externally and must be returned to the source where it has been generated.

Figure 6A:
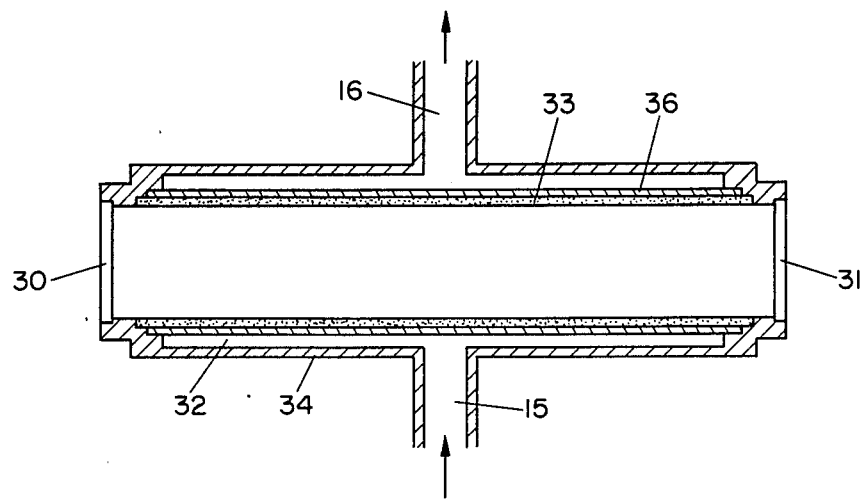
FIGS. 6(a) and 6(b) are views in longitudinal section and cross-section, respectively, illustrating yet another embodiment of an infrared gas analyzer according to the inventor.
Figure 6B:
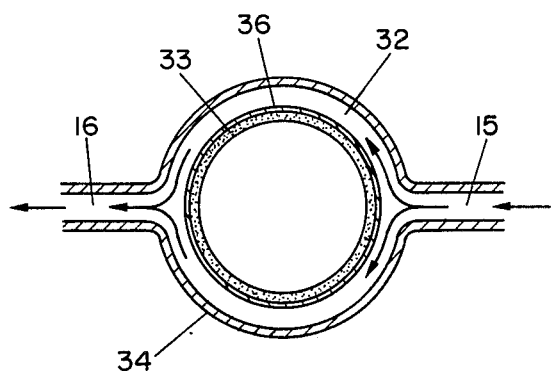

FIG. 6(a) shows the longitudinal section of a fourth example of the measuring cell. In this case the filter 33 is made in layers with a fibrous or sintered tubular layer filter as the inner filter and a coarser filter such as a wire net filter or a coarser sintered filter as the outer layer 36. With this arrangement, classification according to particle sizes will avoid performance reduction which would result from clogging in the filter, thereby prolonging the life of the filter. Although the positions of the inlet 15 and outlet 16 are similar to those shown in FIG. 3(a), they may also be positioned in the manner shown in FIGS. 4(a) and 4(b) or 5(a) and 5(b).

While the described embodiments represent preferred forms of the present invention, it is to be understood that modifications will occur to those skilled in the art without departing from the spirit of the invention. For example, the use of filters having three layers or more, or of sintered metal filters instead of ceramic filters, or of filters which have a shape other than cylindrical is possible, and the measuring cell according to the present invention is applicable to infrared gas analyzers of not only the single-beam type but also the double-beam type.

We claim:

1. An infrared gas analyzer for measuring the concentration of a component of a gas being examined by the infrared absorption of the gas component comprising an infrared radiation source, a measuring cell and an infrared radiation detector, the measuring cell comprising a tubular case having an inlet and outlet for the gas being examined and a tubular filter within the case, the inside wall of the tubular case being concentric with the tubular filter and both ends of the tubular case having infrared transmission windows, the inner wall of the case being spaced from the tubular filter so that the gas being examined is allowed to flow along the periphery of the tubular filter for filtered gas to flow into the interior of the filter, the source and the detector being aligned on opposite ends of the tubular case for directing the infrared radiation to be absorbed longitudinally along the interior of the filter.

2. An infrared gas analyzer according to claim 1 wherein the tubular filter has at least two layers including a porous inner layer and an outer layer with coarser openings than those of the inner layer.

3. An infrared gas analyzer according to claim 2 wherein the inner layer is a fibrous tube.

4. An infrared gas analyzer according to claim 2 wherein the inner layer is a porous sintered tube.

5. An infrared gas analyzer according to claim 2 wherein the outer layer is a tubular wire screen.

6. An infrared gas analyzer according to claim 2 wherein the outer layer is a sintered tube.

* * * * *

UNITED STATES PATENT AND TRADEMARK OFFICE
CERTIFICATE OF CORRECTION

PATENT NO. : 4,622,464
DATED : Nov. 11, 1986
INVENTOR(S) : Sukigara et al.

It is certified that error appears in the above-identified patent and that said Letters Patent is hereby corrected as shown below:

<u>Col. 3, line 66</u>, "filtering." should read --filtering, is divided in half at the inlet 15, each half being directed around the circumference of the tubular gas filter 33, the paths joining at the outlet 16.--.  <u>Col. 4, lines 1-3</u>, delete "is divided in half at the inlet 15, each half being directed around the circumference of the tubular gas filter 33, the paths joining at the outlet 16".

Signed and Sealed this

Twenty-first Day of April, 1987

Attest:

DONALD J. QUIGG

*Attesting Officer*  *Commissioner of Patents and Trademarks*